United States Patent
Otani et al.

(10) Patent No.: US 10,774,234 B2
(45) Date of Patent: Sep. 15, 2020

(54) CELL CULTURE VESSEL

(71) Applicant: NISSAN CHEMICAL INDUSTRIES, LTD., Chiyoda-ku, Tokyo (JP)

(72) Inventors: Ayako Otani, Shiraoka (JP); Taito Nishino, Shiraoka (JP); Yoshiomi Hiroi, Toyama (JP); Takahiro Kishioka, Toyama (JP); Tomoyuki Ozawa, Funabashi (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 523 days.

(21) Appl. No.: 14/896,639

(22) PCT Filed: Jun. 9, 2014

(86) PCT No.: PCT/JP2014/065250
§ 371 (c)(1),
(2) Date: Dec. 7, 2015

(87) PCT Pub. No.: WO2014/196652
PCT Pub. Date: Dec. 11, 2014

(65) Prior Publication Data
US 2016/0115435 A1  Apr. 28, 2016

(30) Foreign Application Priority Data

Jun. 7, 2013 (JP) ................. 2013-121111
Aug. 12, 2013 (JP) ................. 2013-167774

(51) Int. Cl.
| | |
|---|---|
| *C09D 133/14* | (2006.01) |
| *C09D 143/02* | (2006.01) |
| *C12M 1/00* | (2006.01) |
| *C08L 101/02* | (2006.01) |
| *C09D 201/02* | (2006.01) |
| *C08L 43/02* | (2006.01) |
| *C09D 5/16* | (2006.01) |
| *C08F 230/02* | (2006.01) |

(52) U.S. Cl.
CPC .......... *C09D 133/14* (2013.01); *C08F 230/02* (2013.01); *C08L 43/02* (2013.01); *C08L 101/02* (2013.01); *C09D 5/16* (2013.01); *C09D 143/02* (2013.01); *C09D 201/02* (2013.01); *C12M 23/20* (2013.01)

(58) Field of Classification Search
None
See application file for complete search history.

(56) References Cited

U.S. PATENT DOCUMENTS

| | | |
|---|---|---|
| 5,643,561 A | 7/1997 | Katsuen et al. |
| 5,648,442 A | 7/1997 | Bowers et al. |

| | | | |
|---|---|---|---|
| 2008/0081369 A1* | 4/2008 | Adkisson, IV | ...... C12N 5/0655 435/366 |
| 2010/0028286 A1* | 2/2010 | Carballada | ........... A61K 8/8158 424/70.16 |
| 2012/0214230 A1 | 8/2012 | Anneren et al. | |

FOREIGN PATENT DOCUMENTS

| | | |
|---|---|---|
| EP | 2878664 A1 | 6/2015 |
| JP | H04-117276 A | 4/1992 |
| JP | H05-292957 A | 11/1993 |
| JP | H08-140673 A | 6/1996 |
| JP | H11-166015 A | 6/1999 |
| JP | 2003-040937 A | 2/2003 |
| JP | 2007-063459 A | 3/2007 |
| JP | 2008-061609 A | 3/2008 |

(Continued)

OTHER PUBLICATIONS

GB 1110042.7 priority document for WO 2012172291 filed Jun. 14, 2011 (Year: 2011).*

(Continued)

*Primary Examiner* — Susan M Hanley (74) *Attorney, Agent, or Firm* — Leydig, Voit & Mayer, Ltd.

(57) ABSTRACT

The present invention is to provide a cell culture vessel comprising a copolymer which contains a recurring unit containing an organic group of the following formula (a) and a recurring unit containing an organic group of the following formula (b) being coated onto a surface thereof, a method for manufacturing the same and a method for manufacturing a cell aggregate using the same (wherein $U^{a1}$, $U^{a2}$, $U^{b1}$, $U^{b2}$ and $U^{b3}$, and $An^-$ are as defined in the present specification and the claims).

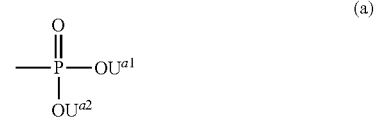

(a)

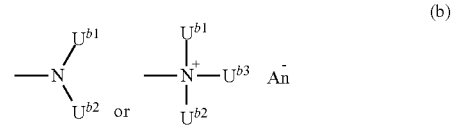

(b)

24 Claims, 1 Drawing Sheet

(56) References Cited

FOREIGN PATENT DOCUMENTS

| WO | WO 2011/049524 A1 | 4/2011 | | |
|----|----|----|----|----|
| WO | WO-2012172291 A1 | * | 12/2012 | ........... C12N 5/0068 |
| WO | WO 2013/144372 A1 | 10/2013 | | |
| WO | WO 2014/017513 A1 | 1/2014 | | |

OTHER PUBLICATIONS

Definition of a varnish downloaded from https://www.dictionary.com/browse/varnish on Feb. 28, 2020 (Year: 2020).*
Japanese Patent Office, International Search Report in International Patent Application No. PCT/JP2014/065250 (dated Aug. 14, 2014).
European Patent Office, Communication Pursuant to Article 94(3) EPC in European Patent Application No. 14808411.4 (dated Mar. 22, 2018).
Japanese Patent Office, Notification of Reasons for Refusal in Japanese Patent Application No. 2015-521514 (dated Mar. 13, 2018).

* cited by examiner

CELL CULTURE VESSEL

CROSS-REFERENCE TO RELATED APPLICATIONS

This patent application is the U.S. national phase of International Patent Application No. PCT/JP2014/065250, filed Jun. 9, 2014, which claims the benefit of Japanese Patent Application No. 2013-167774, filed on Aug. 12, 2013, and Japanese Patent Application No. 2013-121111, filed on Jun. 7, 2013, which are incorporated by reference in their entireties herein.

TECHNICAL FIELD

The present invention relates to a cell culture vessel, a method for manufacturing the same and a method for producing cell aggregate (which is also called as sphere) using the same. In particular, the present invention relates to a cell culture vessel which comprises a copolymer having a function of inhibiting adhesion of biological substances, in particular, cells, being coated on a surface thereof, and a method for manufacturing the same.

BACKGROUND ART

In recent years, a technique for proliferating or maintaining various organs, tissues and cells which play different roles in a living body of an animal or a plant outside the living body has now been developing. To proliferate or maintain these organs and tissues outside the living body are called organ culture and tissue culture, respectively, and to proliferate, differentiate or maintain the cells separated from the organ or the tissue outside the living body is called cell culture. The cell culture is a technique in which the separated cells are proliferating, differentiating or maintaining in a medium outside the living body, and is indispensable for analyzing in detail functions and structures of various kinds of organs, tissues or cells in the living body. Also, the cells and/or the tissues cultured by the technique are utilized in various fields such as evaluation of pharmaceutical effects and toxicity evaluation of chemical substances, medicine, etc., mass production of useful substances such as an enzyme, a cell growth factor, an antibody, regenerative medicine which complements an organ, a tissue or a cell lost by a disease or a defect, breeding of plants, preparation of genetically modified crops, etc.

The cells derived from an animal are roughly divided into two of a floating cell and an adherent cell from their characteristics. The floating cell is a cell which does not require scaffolds for growth and proliferation, while the adherent cell is a cell which requires scaffolds for growth and proliferation, and almost all the cells constituting the living body are the latter adherent cells. As a method for culturing the adherent cells, the monolayer culture, the dispersion culture, the embedding culture, the microcarrier culture and the cell aggregate (sphere) culture, etc., have been known.

In particular, in recent years, accompanying with development in the field of the regenerative medicine, sphere culture has been attracted attention as a culture method which is closer environment to in the living body, and medium compositions or medium additives suitable for the culture have been variously reported (for example, see Patent Documents 1 and 2). Also, in the sphere culture, it has been considered that stimulation from the culture vessel (the substrate) is an important factor which influences the result of the culture, so that it has been required to culture the cells (in particular, a cell aggregate) at a three-dimensional environment or a complete floating condition without any stimulation from the culture vessel (for example, see Patent Document 3).

PRIOR ART DOCUMENTS

Patent Documents

Patent Document 1: WO 2014/017513A
Patent Document 2: WO 2013/144372A
Patent Document 3: JP 2008-61609A

SUMMARY OF THE INVENTION

Problems to be Solved by the Invention

An object of the present invention is to provide a cell culture vessel, a method for manufacturing the same and a method for producing a cell aggregate using the same. In particular, an object of the present invention is to provide a cell culture vessel which comprises a copolymer having a function of inhibiting adhesion of biological substances, in particular, cells being coated onto a surface thereof, a method for manufacturing the same and a method for producing a cell aggregate using the same.

Heretofore, for culturing a cell (in particular, a cell aggregate) in a three-dimensional environment or a complete floating condition, there are problems of adhesion of the cell to the surface (wall surface) of the vessel and elution of a coating applied to a cell culture vessel into a culture solution. In the cell culture vessel to which a coating of a hydrophilic compound has been applied, adhesion of the cells to the surface (wall surface) of the vessel can be reduced, but the problem of elution, etc., of the coating applied to the cell culture vessel into the culture solution has been still remained. In addition, the coating using the hydrophilic compound is not sufficient in resistance to radiation, many of which cannot be sterilized by the radiation after the coating, whereby there is a problem that an aseptic production is required.

Means for Solving the Problems

The present inventors have earnestly studied by attracting a polymer having a phosphoric acid ester group which has been expected to be a coating material having a function of inhibiting adhesion of various biological substances. As a result, they have found that a cell culture vessel at least a part of a surface of which has been coated by a copolymer containing a specific organic group inhibits adhesion of the cells to the surface (wall surface) of the vessel as well as the coating can be firmly fixed onto the surface of the vessel, so that it is useful as a cell culture vessel improved in elution of the coating into the culture solution and radiation resistance, whereby the present invention has been accomplished.

That is, the present inventions are as follows:

1. a cell culture vessel comprising a copolymer which contains a recurring unit containing an organic group of the following formula (a) and a recurring unit containing an organic group of the following formula (b):

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms and $An^-$ represents an anion selected from the group consisting of a halide ion, an inorganic acid ion, a hydroxide ion and an isothiocyanate ion) being coated onto a surface thereof;

2. the cell culture vessel described in the above-mentioned 1, wherein the recurring units containing organic groups of the above-mentioned formulae (a) and (b) are recurring units derived from monomers of the following formulae (A) and (B), respectively:

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), $An^-$ represents an anion selected from the group consisting of a halide ion, an inorganic acid ion, a hydroxide ion and an isothiocyanate ion, and m is an integer of 0 to 6);

3. the cell culture vessel described in the above-mentioned 2, wherein m is 1, and $R^a$ and $R^b$ each independently represent an ethylene group or a propylene group;

4. the cell culture vessel described in any one of the above-mentioned 1 to 3, wherein the copolymer further contains a crosslinked structure derived from a monomer of the following formula (C) or (D):

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s));

5. the cell culture vessel described in the above-mentioned 4, wherein $T^c$ and $T^d$ each independently represent a hydrogen atom or a methyl group, $U^d$ represents a hydrogen atom, $R^c$ and $R^d$ each independently represent an ethylene group or a propylene group;

6. a method for manufacturing a cell culture vessel comprising a process of coating a copolymer which contains a recurring unit containing an organic group of the following formula (a) and a recurring unit containing an organic group of the following formula (b):

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms and $An^-$ represents an anion selected from the group consisting of a halide ion, an inorganic acid ion, a hydroxide ion and an isothiocyanate ion) onto at least a part of a surface of the vessel; and a process of drying the coated vessel at −200° C. to 200° C.;

8. the manufacturing method described in the above-mentioned 6, wherein the recurring units containing organic groups of the above-mentioned formulae (a) and (b) are recurring units derived from monomers of the following formulae (A) and (B), respectively:

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), $An^-$ represents an anion selected from the group consisting of a halide ion, an inorganic acid ion, a hydroxide ion and an isothiocyanate ion, and m is an integer of 0 to 6);

8. the manufacturing method described in the above-mentioned 6 or 7, wherein the coating process is carried out by using a varnish containing the copolymer;

9. the manufacturing method described in the above-mentioned 8, wherein the varnish containing the copolymer is previously pH adjusted;

10. the manufacturing method described in any one of the above-mentioned 6 to 9, wherein the method further comprises a process of washing the coated cell culture vessel before and/or after the drying process;

11. the manufacturing method described in the above-mentioned 10, wherein the washing after the drying process is carried out by using at least one solvent selected from the group consisting of water and an aqueous solution containing an electrolyte(s);

12. the manufacturing method described in any one of the above-mentioned 6 to 11, wherein the method further comprises a process of sterilizing the coated cell culture vessel by a radiation treatment after the drying;

13. a method for producing a cell aggregate comprising using a cell culture vessel described in any one of the above-mentioned 1 to 5 or a cell culture vessel manufactured by the manufacturing method described in any one of the above-mentioned 6 to 12;

14. the producing method of a cell aggregate described in the above-mentioned 13, wherein a medium in the cell culture vessel contains a polysaccharide having an effect of floating cells or tissues;

15. the producing method of a cell aggregate described in the above-mentioned 14, wherein the polysaccharide is deacylated gellan gum.

Effect of the Invention

In the cell culture vessel of the present invention, adhesion of the cells to the surface (wall surface) of the vessel can be inhibited by using a vessel at least a part of the surface of which is coated by a copolymer containing a specific organic group. The cell culture vessel of the present invention is coated by the copolymer containing an anion of the formula (a) and a cation of the formula (b) onto at least a part of the surface of the vessel, so that the surface of the vessel is maintained to electrically neutral by the electrostatic balance between the cation and the anion, whereby adhesion of the cells can be considered to be inhibited. On the other hand, by forming an ionic bonding (ion complex) with the cation and the anion in the coating, it can be firmly fixed irrespective of a kind of the substrate such as glass, fiber, inorganic particles and a resin (a synthetic resin and a natural resin), and further, after fixing, it becomes a coating excellent in durability against an aqueous solvent (water, a phosphate buffered solution (PBS), an alcohol, etc.). Also, such a coating is excellent in radiation resistance, whereby sterilization by radiation can be carried out. That is, according to the present invention, a cell culture vessel excellent in durability to the solvent and radiation in addition to inhibition of adhesion of cells can be provided.

BRIEF EXPLANATION OF THE DRAWINGS

FIG. 2 (a) shows a microscopic photograph (magnification: 40-fold) of an aggregate of HepG2 cells cultured in a medium to which no deacylated gellan gum has been added in a flat bottom plate coated by the surface treatment agent L1 obtained in Test example 3. FIG. 2 (b) shows a microscopic photograph (magnification: 40-fold) of an aggregate of HepG2 cells cultured in a medium to which deacylated gellan gum has been added in a flat bottom plate coated by the surface treatment agent L1 obtained in Test example 3.

EMBODIMENTS TO CARRY OUT THE INVENTION

Cell Culture Vessel

The first embodiment of the present invention is directed to a cell culture vessel comprising a copolymer which contains a recurring unit containing an organic group of the following formula (a) and a recurring unit containing an organic group of the following formula (b):

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms and $An^-$ represents an anion selected from the group consisting of a halide ion, an inorganic acid ion, a hydroxide ion and an isothiocyanate ion) being coated onto a surface thereof.

<Cell>

The cell mentioned in the present invention means the most basic unit constituting an animal or a plant, and has cytoplasm and various kinds of organelles at the inside of the cell membrane as elements. At this time, a nucleus including DNA may be or may not be contained at the inside of the cell. For example, the cells originated from an animal in the present invention include germ cells such as spermatozoa and ova, somatic cell constituting a living body, stem cells (pluripotent stem cells, etc.), precursor cells, cancer cells separated from a living body, cells (cell lines) separated from a living body and stably maintained outside the body by gaining an immortalization ability, cells separated from a living body and artificially gene-modified, cells separated from a living body and the nucleus of which is artificially exchanged, etc. Examples of the somatic cell constituting a living body include, but not limited only to the following: fibroblast, bone marrow cells, B lymphocytes, T lymphocytes, neutrophils, red blood cells, platelets, macrophages, monocytes, bone cells, bone marrow cells, perithelial cells, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocyte, microglia, astroglial cells, heart cells, esophagus cells, muscle cells (for example, smooth muscle cells or skeletal muscle cells), pancreatic beta cells, melanocytes, hematopoietic precursor cells (for example, CD34 positive cells derived from cord blood), and mononuclear cells, etc. The said somatic cell may include, for example, cells collected from an optional tissue such as skin, kidney, spleen, adrenal gland, liver, lung, ovary, pancreas, uterus, stomach, colon, small intestine, large intestine, bladder, prostate, testis, thymus, muscle, connective tissue, bone, cartilage, vascular tissue, blood (including cord blood), bone marrow, heart, eye, brain or nerve tissue, etc. The stem cell means a cell having both of an ability of replicating itself and an ability of differentiating to the other multiple cell lines, and examples thereof include, but not limited only to the following: embryonic stem cells (ES cell), embryonic tumor cells, embryonic germline stem cells, induced pluripotent stem cells (iPS cell), neural stem cells, hematopoietic stem cells, mesenchymal stem cells, liver stem cells, pancreatic stem cells, muscle stem cells, germline stem cells, intestinal stem cells, cancer stem cells, hair follicle stem cells, etc. The pluripotent stem cells may be mentioned, among the above-mentioned stem cells, ES cells, embryonic germline stem cells and iPS cells. The precursor cells are cells in a halfway stage of differentiating from the above-mentioned stem cells to specific somatic cells or germ cells. The cancer cells are cells gained infinite proliferation ability derived from somatic cells. The cell lines are cells gained infinite proliferation ability by artificial operation outside the living body. Examples of the cancer cell lines include, but not limited only to the following: human breast cancer cell lines such as HBC-4, BSY-1, BSY-2, MCF-7, MCF-7/ADR RES, HS578T, MDA-MB-231, MDA-MB-435, MDA-N, BT-549 and T47D, human cervical cancer cell lines such as HeLa, human lung cancer cell lines such as A549, EKVX, HOP-62, HOP-92, NCI-H23, NCI-H226, NCI-H322M, NCI-H460, NCI-H522, DMS273 and DMS114, human colorectal cancer cell lines such as Caco-2, COLO-205, HCC-2998, HCT-15, HCT-116, HT-29, KM-12, SW-620 and WiDr, human prostate cancer cell lines such as DU-145, PC-3 and LNCaP, human central nervous system cancer cell lines such as U251, SF-295, SF-539, SF-268, SNB-75, SNB-78 and SNB-19, human ovarian cancer cell lines such as OVCAR-3, OVCAR-4, OVCAR-5, OVCAR-8, SK-OV-3 and IGROV-1, human kidney cancer cell lines such as RXF-631L, ACHN, UO-31, SN-12C, A498, CAKI-1, RXF-393L, 786-0 and TK-10, the human stomach cancer cell lines such as MKN45, MKN28, St-4, MKN-1, MKN-7 and MKN-74, skin cancer cell lines such as LOX-IMVI, LOX, MALME-3M, SK-MEL-2, SK-MEL-5, SK-MEL-28, UACC-62, UACC-257 and M14, leukemia cell lines such as CCRF-CRM, K562, MOLT-4, HL-60 TB, RPMI8226, SR, UT7/TPO and Jurkat, etc. Examples of the cell lines include, but not limited only to the following: HEK293 (human embryonal kidney cells), MDCK, MDBK, BHK, C-33A, AE-1, 3D9, Ns0/1, NIH3T3, PC12, S2, SD, Sf9 Sf21, High Five (Registered Trademark) and Vero, etc. Examples of liver cell lines include, but not limited only to the following: HepG2, Hep3B, HepaRG (Registered Trademark), JHH7, HLF, HLE, PLC/PRF/5, WRL68, HB611, SK-HEP-1, HuH-4 and HuH-7, etc.

The cells originated from a plant according to the present invention include a cell separated from each tissue of plants and a protoplast in which cellular walls are artificially removed from the cell, too.

<Vessel>

The vessel onto which the copolymer has been coated, which constitutes the cell culture vessel of the present invention, may be any vessels with an optional shape which can be used in this field of the art and may be mentioned, for example, a culture dish, a flask, a plastic bag, a Teflon (Registered Trademark) bag, a dish, a petri dish, a dish for tissue culture, a multi dish, a microplate, a microwell plate, a multiplate, a multi-well plate, a chamber slide, a cell culture flask, a spinner flask, a tube, a tray, a culture bag, a roller bottle, etc., which are generally used in culturing cells. It is preferably mentioned a 6 to 1536-well multi-well plate and a culture dish.

As a raw material of the vessel, glass or a resin may be typically used. In the points of easiness in working and economic efficiency, etc., a resin is preferably used. The resin may be either a natural resin or a synthetic resin, and the natural resin may be mentioned, for example, cellulose, cellulose triacetate (CTA), cellulose to which dextran sulfate has been fixed, etc., while the synthetic resin may be mentioned, for example, a polyacrylonitrile (PAN), a polyester-based polymer alloy (PEPA), a polystyrene (PS), a polysulfone (PSF), a polyethylene terephthalate (PET), a polymethyl methacrylate (PMMA), a polyvinyl alcohol (PVA), a polyurethane (PU), ethylene vinyl alcohol (EVAL), a polyethylene (PE), a polyester (PE), a polypropylene (PP), a polyvinylidene fluoride (PVDF), various kinds of ion exchange resins or a polyether sulfone (PES), etc. In the manufacture of the cell culture vessel of the present invention, when the copolymer is to be coated to present onto at least a part of the surface of the vessel, no treatment at the high temperature is required, so that a resin having low heat resistance, etc., can be also applied thereto.

<Copolymer>

The cell culture vessel of the present invention comprises a specific copolymer being coated onto at least a part of a surface of the vessel. The copolymer according to the present invention is a copolymer which contains a recurring unit containing an organic group of the following formula (a) and a recurring unit containing an organic group of the following formula (b):

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms and $An^-$ represents an anion selected from the group consisting of a halide ion, an inorganic acid ion, a hydroxide ion and an isothiocyanate ion).

The copolymer according to the present invention is not particularly limited so long as it is a copolymer which contains a recurring unit containing an organic group of the above-mentioned formula (a) and a recurring unit containing an organic group of the above-mentioned formula (b). The copolymer is desirably a material obtained by subjecting a monomer containing an organic group of the above-mentioned formula (a) and a monomer containing an organic group of the above-mentioned formula (b) to radical polymerization, and a material obtained by polycondensation or polyaddition reaction may be also used. Examples of the copolymer include a vinyl polymerized polymer in which an olefin(s) is/are reacted, a polyamide, a polyester, a polycarbonate, a polyurethane, and among these, a vinyl polymerized polymer in which an olefin(s) is/are reacted or a (meth)acrylic polymer in which a (meth)acrylate compound(s) is/are polymerized is desired. Further, in the present invention, the (meth)acrylate compound means both of an acrylate compound and a methacrylate compound. For example, a (meth)acrylic acid means an acrylic acid and a methacrylic acid.

The monomers containing the organic groups of the above-mentioned formulae (a) and (b) are preferably monomers of the following formulae (A) and (B), respectively:

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), $An^-$ represents an anion selected from the group consisting of a halide ion, an inorganic acid ion, a hydroxide ion and an isothiocyanate ion, and m is an integer of 0 to 6). Accordingly, the recurring units derived from the monomers of the formulae (A) and (B) are of the following formulae (a1) and (b1), respectively:

(wherein $T^a$, $T^b$, $U^{a1}$, $U^{a2}$, $U^{b1}$, $U^{b2}$ and $U^{b3}$, $Q^a$ and $Q^b$, $R^a$ and $R^b$, $An^-$ and m have the same meanings as defined above).

In the present invention, "the linear or branched alkyl group having 1 to 5 carbon atoms" may be mentioned, for example, a methyl group, an ethyl group, an n-propyl group, an isopropyl group, an n-butyl group, an isobutyl group, a s-butyl group, a t-butyl group, an n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group.

In the present invention, "the ester bond" means —C(=O)—O— or —O—C(=O)—, and "the amide bond" means —NHC(=O)— or —C(=O)NH—.

In the present invention, "the linear or branched alkylene group having 1 to 10 carbon atom which may be substituted by a halogen atom(s)" means a linear or branched alkylene group having 1 to 10 carbon atoms or a linear or branched alkylene group having 1 to 10 carbon atoms substituted by one or more halogen atoms. Here, "the linear or branched alkylene group having 1 to 10 carbon atoms" is a divalent organic group in which a hydrogen atom is further removed from the above-mentioned alkyl group and may be mentioned, for example, a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyl-tetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc. Among these, an ethylene group, a propylene group, an octamethylene group and a decamethylene group are preferred, a linear or branched alkylene group having 1 to 5 carbon atoms including, for example, an ethylene group, a propylene group, a trimethylene group and a tetramethylene group are more preferred, and an ethylene group or a propylene group is particularly preferred. "The linear or branched alkylene group having 1 to 10 carbon atoms substituted by one or more halogen atoms" means a group in which one or more optional hydrogen atoms of such an alkylene group is/are substituted by a halogen atom(s), and particularly preferred is a group in which a part or whole of the hydrogen atoms of an ethylene group or a propylene group is/are substituted by a halogen atom(s).

In the present invention, "the halogen atom" may be mentioned a fluorine atom, a chlorine atom, a bromine atom and an iodine atom.

In the present invention, "the halide ion" means an anion of a halogen atom, and may be mentioned a fluoride ion, a chloride ion, a bromide ion and an iodide ion, preferably a chloride ion.

In the present invention, "the inorganic acid ion" means a carbonate ion, a sulfate ion, a phosphate ion, a hydrogen phosphate ion, a dihydrogen phosphate ion, a nitrate ion, a perchlorate ion or a borate ion.

As the above-mentioned $An^-$, preferred are a halide ion, a sulfate ion, a phosphate ion, a hydroxide ion and an isothiocyanate ion, and particularly preferred is a halide ion.

In the formulae (A) and (B), $T^a$ and $T^b$ are preferably each independently a hydrogen atom, a methyl group or an ethyl group, and more preferably each independently a hydrogen atom or a methyl group.

In the formula (a), the formula (b), and the formulae (A) and (B), $U^{a1}$, $U^{a2}$, $U^{b1}$, $U^{b2}$ and $U^{b3}$ are preferably each independently a hydrogen atom, a methyl group or an ethyl group. In the formula (a) and the formula (A), $U^{a1}$ and $U^{a2}$ are more preferably a hydrogen atom. In the formulae (b) and (B), $U^{b1}$, $U^{b2}$ (and $U^{b3}$) are more preferably a methyl group or an ethyl group, and particularly preferably a methyl group.

In the formulae (A) and (B), $Q^a$ and $Q^b$ preferably each independently represent an ester bond (—C(═O)—O— or —O—C(═O)—) or an amide bond (—NHC(═O)— or —C(═O)NH—), more preferably each independently represent —C(═O)—O— or —C(═O)NH—, particularly preferably —C(═O)—O—.

In the formulae (A) and (B), $R^a$ and $R^b$ each preferably independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group.

In the formulae (A) and (B), m is preferably an integer of 0 to 3, more preferably an integer of 1 or 2, particularly preferably 1.

Specific examples of the above-mentioned formula (A) include vinyl phosphonic acid, acid phosphoxy ethyl (meth) acrylate, 3-chloro-2-acid phosphoxypropyl (meth)acrylate, acid phosphoxypropyl (meth)acrylate, acid phosphoxymethyl (meth)acrylate, acid phosphoxypolyoxyethylene glycol mono(meth)-acrylate, acid phosphoxypolyoxypropylene glycol mono(meth)acrylate, etc., and among these, vinyl phosphonic acid, acid phosphoxy ethyl methacrylate (=2-(methacryloyl-oxy)ethyl phosphate) is preferably used.

The structural formulae of the vinyl phosphonic acid, acid phosphoxyethyl methacrylate (=2-(methacryloyloxy)ethyl phosphate) and acid phosphoxypolyoxyethylene glycol monomethacrylate are shown by the following formula (A-1) to the formula (A-3), respectively.

These compounds may contain a (meth)acrylate compound having two functional groups of the formula (C) or (D) mentioned later at the time of synthesis in some cases.

Specific examples of the above-mentioned formula (B) include dimethylaminoethyl (meth)acrylate, diethylaminoethyl (meth)acrylate, dimethylaminopropyl (meth)acrylate, 2-(t-butylamino)ethyl (meth)acrylate, methacryloylcholine chloride, and among these, dimethylaminoethyl (meth)acrylate, methacryloylcholine chloride or 2-(t-butylamino)ethyl (meth)acrylate is preferably used.

Structural formulae of the dimethylaminoethyl acrylate (=acrylic acid 2-(dimethylamino)ethyl), dimethylaminoethyl methacrylate (=methacrylic acid 2-(dimethylamino) ethyl), methacryloylcholine chloride and 2-(t-butylamino) ethyl methacrylate (=methacrylic acid 2-(t-butylamino)ethyl are shown by the following formula (B-1) to the formula (B-4), respectively.

A ratio of the recurring unit containing an organic group of the formula (a) (or a recurring unit of the formula (a1)) in the above-mentioned copolymer is 20 mol % to 80 mol %, preferably 30 mol % to 70 mol %, more preferably 40 mol % to 60 mol %. Further, the copolymer according to the present invention may contain two or more kinds of the recurring unit containing an organic group of the formula (a) (or the recurring units of the formula (a1)).

A ratio of the recurring unit containing an organic group of the formula (b) (or a recurring unit of the formula (b1)) in the above-mentioned copolymer according to the present invention may be the whole remainder subtracting the ratio of the above-mentioned formula (a) (or the formula (a1)) from the whole of the copolymer, or may be the remainder subtracting the total ratio of the above-mentioned formula (a) (or the formula (a1)) and a third component mentioned below from the same. Further, the copolymer according to the present invention may contain two or more kinds of the recurring units containing an organic group of the formula (b) (or a recurring unit of the formula (b1)).

Further, the copolymer according to the present invention may be further copolymerized with an optional third component. For example, as the third component, a (meth) acrylate compound having two or more functional groups may be copolymerized, and a part of the polymer may be partially three-dimensionally crosslinked. Such a third component may be mentioned, for example, a bifunctional monomer of the following formula (C) or (D):

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s)). That is, the copolymer according to the present invention may preferably contain a crosslinked structure derived from such a bifunctional monomer.

In the formulae (C) and (D), $T^c$ and $T^d$ are preferably each independently a hydrogen atom, a methyl group or an ethyl group, and more preferably each independently a hydrogen atom or a methyl group.

In the formulae (C) and (D), $U^d$ is preferably a hydrogen atom, a methyl group or an ethyl group, more preferably a hydrogen atom.

In the formulae (C) and (D), $R^c$ and $R^d$ each preferably independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group.

The bifunctional monomer of the formula (C) may be preferably mentioned ethylene glycol di(meth)acrylate, triethylene glycol di(meth)acrylate, propylene glycol di(meth) acrylate, etc. The bifunctional monomer of the formula (D) may be preferably mentioned bis[(2-methacryloyloxy) methyl]phosphate, bis[(2-methacryloyloxy)ethyl]phosphate, bis[(2-methacryloyloxy)propyl]phosphate, etc.

The optional third component may be a trifunctional monomer. Such a trifunctional monomer as the third component may be mentioned, for example, phosphynylidine tris(oxy-2,1-ethane diyl)triacrylate.

Among these, ethylene glycol di(meth)acrylate of the following formula (C-1) and bis[2-(methacryloyloxy)ethyl] phosphate of the following formula (D-1) are particularly preferred.

One or two or more kinds of these third components may be contained in the copolymer. Among the above-mentioned compounds, the bifunctional monomer of the formula (D) is preferred, and the bifunctional monomer of the formula (D-1) is particularly preferred.

A ratio of the third component in the above-mentioned copolymer, for example, cross-linked structure derived from the bifunctional monomer of the above-mentioned formula (C) or (D) is 0 mol % to 50 mol %.

<Manufacturing Method of Copolymer>

As the synthetic method of the copolymer according to the present invention, they can be synthesized by the methods such as the radical polymerization, the anion polymerization, the cation polymerization, which are general synthetic methods of an acrylic polymer or a methacrylic polymer, etc. As the reaction form thereof, various methods such as the solution polymerization, the suspension polymerization, the emulsion polymerization, the bulk polymerization may be employed.

As the solvent for the reaction, it may be water, a phosphate buffered solution or an alcohol such as ethanol, etc., or a mixed solution in which these solvents are used in combination, and desirably contains water or ethanol. Further, it is preferred to contain water or ethanol in an amount of 10% by mass or more and 100% by mass or less. Moreover, it is preferred to contain water or ethanol in an amount of 50% by mass or more and 100% by mass or less. Furthermore, it is preferred to contain water or ethanol in an amount of 80% by mass or more and 100% by mass or less. Still further, it is preferred to contain water or ethanol in an amount of 90% by mass or more and 100% by mass or less. A total amount of water and ethanol is preferably 100% by mass.

As the reaction concentration, for example, it is preferred to make the concentration of the monomer containing an organic group of the above-mentioned formula (a) and the monomer containing an organic group of the above-mentioned formula (b) in the reaction solvent 0.01% by mass to 4% by mass. If the concentration is 4% by mass or more, for example, there is sometimes a case that the copolymer is gelled in the reaction solvent due to strong associative property possessed by the phosphate group of the formula (a). If the concentration is 0.01% by mass or less, the concentration of the obtained varnish is too low, it is difficult to prepare the composition for forming a coating film for obtaining a coating film having a sufficient film thickness. The concentration is more preferably 0.01% by mass to 3% by mass, for example, 3% by mass or 2% by mass.

In the synthesis of the copolymer according to the present invention, for example, after preparing an acidic phosphoric acid ester monomer (half salt) of the formula (1), it may be polymerized to prepare the copolymer.

(1)

The phosphate group-containing monomer is a monomer easily associated, so that it may be added dropwise to the reaction solvent little by little so as to rapidly disperse therein when it is added dropwise to the reaction system. Further, the reaction solvent may be heated (for example, 40° C. to 100° C.) to increase the solubility of the monomer and the polymer.

To proceed with the polymerization reaction efficiently, a polymerization initiator is desirably used. Examples of the polymerization initiator to be used include 2,2'-azobis (isobutyronitrile), 2,2'-azobis(2-methylbutyronitrile), 2,2'-azobis(2,4-dimethylvaleronitrile), 4,4'-azobis(4-cyanovaleric acid), 2,2'-azobis(4-methoxy-2,4-dimethylvaleronitrile), 1,1'-azobis(cyclohexan-1-carbonitrile), 1-[(1-cyano-1-methylethyl)azo]formamide, 2,2'-azobis[2-(2-imidazolin-2-yl)propane]dihydrochloride, 2,2'-azobis[2-(2-imidazolin-2-yl)propane], 2,2'-azobis(2-methylpropionamidine)dihydrochloride, 2,2'-azobis[(2-methyl-N-(2-hydroxyethyl)propionamide] (available from Wako Pure Chemical Industries, Ltd., VA-086, 10-hr half-life temperature; 86° C.), benzoyl peroxide (BPO), 2,2'-azobis(N-(2-carboxyethyl)-2-methylpropionamidine) n-hydrate (available from Wako Pure Chemical Industries, Ltd., VA-057, 10-hr half-life temperature; 57° C.), 4,4'-azobis(4-cyanopentanoic acid) (available from Wako Pure Chemical Industries, Ltd., VA-501), 2,2'-azobis[2-(2-imidazolidin-2-yl)propane]dihydrochloride (available from Wako Pure Chemical Industries, Ltd., VA-044, 10-hr half-life temperature; 44° C.), 2,2'-azobis[2-(2-imidazolidin-2-yl)propane] disulfate dihydrate (available from Wako Pure Chemical Industries, Ltd., VA-046B, 10-hr half-life temperature; 46° C.), 2,2'-azobis[2-(2-imidazolidin-2-yl)propane] (available from Wako Pure Chemical Industries, Ltd., VA-061, 10-hr half-life temperature; 61° C.), 2,2'-azobis(2-amidinopropane)dihydrochloride (available from Wako Pure Chemical Industries, Ltd., V-50, 10-hr half-life temperature; 56° C.), peroxodisulfate or t-butyl hydroperoxide, and among these, taking ion balance and solubility in water into consideration, it is desired to use any of 2,2'-azobis[(2-methyl-N-(2-hydroxyethyl)-propionamide], 2,2'-azobis[N-(2-carboxyethyl)-2-methylpropionamidine]n-hydrate, 4,4'-azobis(4-cyanopentanoic acid), 2,2'-azobis[2-(2-imidazolidin-2-yl) propane]dihydrochloride, 2,2'-azobis[2-(2-imidazolidin-2-yl)propane]disulfate dihydrate, 2,2'-azobis[2-(2-imidazolidin-2-yl)propane], 2,2'-azobis(2-amidinopropane) dihydrochloride and peroxodisulfate.

An amount of the polymerization initiator to be added is 0.05% by mass to 10% by mass based on the total weight of the monomer to be used for the polymerization.

As the reaction conditions, the polymerization reaction proceeds by heating a reaction vessel by an oil bath, etc., at 50° C. to 200° C. and stirring for 1 hour to 48 hours, more preferably at 80° C. to 150° C. for 5 hours to 30 hours to obtain the copolymer of the present invention. The reaction atmosphere is preferably a nitrogen atmosphere. As the reaction procedure, the whole reaction substances are charged in the reaction solvent at the room temperature, and then, the polymerization may be carried out by heating to the above-mentioned temperature, or whole or a part of the mixture of the reaction substances may be added dropwise to the previously heated solvent little by little.

For example, as the latter reaction procedure, a mixture containing the compounds of the above-mentioned formulae (A) and (B), a solvent and a polymerization initiator is added dropwise into a solvent which has been maintained at a temperature higher than a 10-hr half-life temperature of the polymerization initiator to react (polymerize) the reactants. By employing such a reaction procedure and temperature conditions, a concentration of the compounds of the above-mentioned formulae (A) and (B) in the reaction solvent can be made, for example, 0.01% by mass to 10% by mass. In this case, even if the concentration exceeds 4% by mass, the dropping phase and the reaction phase become a transparent uniform solution before the reaction, and gelation of the copolymer in the reaction solvent after the reaction can be suppressed.

A molecular weight of the copolymer according to the present invention may be several thousand to several million or so, preferably 5,000 to 5,000,000. It is more preferably 10,000 to 2,000,000. Also, it may be either of a random copolymer, a block copolymer or a graft copolymer, there is no specific limitation in the copolymerization reaction itself for manufacturing the copolymer, and a conventionally known method synthesized in a solution such as radical polymerization, ion polymerization, or polymerization utilizing photopolymerization, macromer or emulsion polymerization can be used. Depending on the purposes thereof to be used, any one of the copolymers of the present invention may be solely used, or plural kinds of the copolymers may be used by mixing with appropriately changing the ratios thereof.

The various copolymers manufactured as mentioned above may be a two-dimensional polymer or a three-dimensional polymer, and is in a state of dispersing in a solution containing water. That is, in the varnish containing these polymers, it is not preferred to cause ununiform gelation or turbid precipitation, and a transparent varnish, a dispersed colloidal varnish or a sol is preferred.

<<Manufacturing Method of Cell Culture Vessel>>

The second embodiment of the present invention is directed to a method for manufacturing a cell culture vessel comprising a process of coating a copolymer which contains a recurring unit containing an organic group of the following formula (a) and a recurring unit containing an organic group of the following formula (b):

(wherein $U^{a1}$, $U^{a2}$, $U^{b1}$, $U^{b2}$ and $U^{b3}$, and $An^-$ have the same meanings as defined above) onto at least a part of a surface of a vessel; and a process of drying the coated vessel at −200° C. to 200° C.

<Coating Process>

In the coating process of the manufacturing method of a cell culture vessel of the present invention, the copolymer is coated onto at least a part of the surface of the vessel. For example, when the vessel is a round bottom multi-well plate, only the recessed portion of the well may be coated, or the whole plate may be coated. Here, the vessel and the copolymer are the same as mentioned in the above-mentioned items <Vessel> and <Copolymer>.

The coating process is not specifically limited, and may be carried out by any of the coating means (for example, coating, dipping, etc.) well known for those skilled in the art which can contact the vessel with the copolymer. It may be carried out, for example, by coating a varnish containing the copolymer onto the vessel, or by dipping the vessel in a varnish containing the copolymer. It is preferably carried out by dipping the vessel into the varnish containing the copolymer.

The varnish containing the copolymer may be prepared by dissolving the copolymer obtained by the above-mentioned item <Manufacturing method of copolymer> in a suitable solvent with a desired concentration, or the reaction solution containing the copolymer obtained by such a manufacturing method may be used as a varnish as such or after diluting in a desired solid content. The solvent contained in the varnish may be mentioned water, a phosphate buffered solution (PBS) and an alcohol. Examples of the alcohol include an alcohol having 2 to 6 carbon atoms such as ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (=neopentyl alcohol), 2-methyl-1-propanol, 2-methyl-1-butanol, 2-methyl-2-butanol (=t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol. The solvent may be used alone or a mixed solvent of a combination thereof, and preferably selected from water, PBS and ethanol. For dissolving the copolymer, water is necessarily contained.

A concentration of the copolymer in the varnish is 0.01 to 4% by mass, more desirably 0.01 to 3% by mass, further desirably 0.01 to 2% by mass, and still further desirably 0.01 to 1% by mass. If the concentration of the copolymer is 0.01% by mass or less, a coating film having a sufficient film thickness cannot be formed, while if it is 4% by mass or more, storage stability of the varnish is poor, and there is a possibility of causing deposition of the dissolved material or gelation thereof.

Further, to the varnish may be added other substances within the range which does not impair the performance of the obtainable coating depending on the necessity, in addition to the above-mentioned copolymer and the solvent. The other substances may be mentioned an antiseptic, a surfactant, a primer which heighten adhesiveness with the substrate (the vessel), an antifungal agent and a saccharide, etc.

To control ion balance of the copolymer in the varnish, a pH of the varnish containing the copolymer may be previously adjusted. The pH adjustment may be carried out, for example, by adding a pH adjusting agent to the varnish containing the copolymer, to make the pH of the varnish 3.5 to 8.5, more preferably 4.0 to 8.0. A kind of the pH adjusting agent which can be used and an amount thereof are appropriately selected depending on the concentration of the copolymer in the varnish, and an existing ratio of the anion and the cation of the copolymer, etc. Examples of the pH adjusting agent include an organic amine such as ammonia, diethanolamine, pyridine, N-methyl-D-glucamine, tris(hydroxymethyl)aminomethane; an alkali metal hydroxide such as potassium hydroxide, sodium hydroxide; an alkali metal halide such as potassium chloride, sodium chloride; an inorganic acid such as sulfuric acid, phosphoric acid, hydrochloric acid, carbonic acid or an alkali metal salt thereof; a quaternary ammonium cation such as choline or a mixture thereof (for example, a buffer such as a phosphate buffered physiological saline). Among these, ammonia, diethanolamine, N-methyl-D-glucamine, tris(hydroxymethyl)aminomethane, sodium hydroxide and choline are preferred, and ammonia, diethanolamine, sodium hydroxide and choline are particularly preferred.

The varnish containing such a copolymer is contacted with the vessel to form a coating onto at least a part of the surface thereof. The coating is desirably formed over the whole surface of the vessel.

Further, before the coating process, the surface of the vessel may be washed by applying it to the conventionally known UV/ozone treatment. Such a washing process can be carried out by using a commercially available UV/ozone cleaner, etc.

<Drying, Washing and Sterilization Process>

After the coating process, the coated vessel is dried at a temperature of −200° C. to 200° C. According to the drying, the solvent in the above-mentioned composition for forming the coating film is removed, as well as the formula (a) and the formula (b) of the copolymer according to the present invention form an ionic bonding to each other whereby the film is completely and firmly fixed to the substrate. A film thickness of the coating film of the vessel of the present invention is preferably 10 to 1,000Å, more preferably 10 to 500 Å. The present inventors have found that according to the manufacturing method of the cell culture vessel of the present invention, a coating having desired characteristics is formed onto the surface of the vessel by a treatment at a low temperature without requiring a treatment at a high temperature, and yet, in spite of a thin film thickness of several ten to several hundred Å or so, it is excellent in durability.

The drying may be carried out, for example, at room temperature (10° C. to 35° C., for example, 25° C.), and for forming a coating film more rapidly, it may be carried out, for example, at 40° C. to 50° C. In addition, it may be carried out at a very low temperature to low temperature (−200° C. to around −30° C.) by a freeze drying method. Freeze drying is called as freeze vacuum drying, and is a method of removing a solvent under a vacuum state by sublimation while generally cooling a material to be dried with a coolant. A general coolant to be used in the freeze drying may be mentioned a mixed medium of dry ice and methanol (−78° C.), liquid nitrogen (−196° C.), etc. More preferred drying temperature is 10° C. to 180° C., and more preferred drying temperature is 25° C. to 150° C.

Further, before and/or after the drying process, the surface of the coated vessel may be washed with an alcohol having 1 to 5 carbon atoms such as ethanol and/or water. Such a washing process may be carried out at a temperature of 0° C. to 60° C., preferably 25° C. (room temperature) to 40° C. for 30 minutes to 48 hours, preferably 1 to 24 hours.

Further, after the drying process, to remove impurities, unreacted monomer, etc., remained onto the coating, and further to adjust ion balance of the copolymer in the film, it may be washed with flowing water or washing with ultrasonic wave, etc., using at least one solvent selected from the group consisting of water and an aqueous solution containing an electrolyte(s). Here, the water and the aqueous solution containing an electrolyte(s) may be heated, for example, within the range of 40° C. to 95° C. The aqueous solution containing an electrolyte(s) is preferably PBS, a physiological saline (a solution containing sodium chloride alone), a Dulbecco's phosphate buffered physiological saline, a Tris buffered physiological saline, a HEPES buffered physiological saline and a Veronal buffered physiological saline, and PBS is particularly preferred.

Even when the coating is washed with an alcohol, water and PBS, etc., it does not elute and is still firmly fixed to the substrate (i.e., the vessel). The formed coating has a function of inhibiting adhesion of various biological substances including cells. Accordingly, the cell culture vessel of the present invention is excellent in durability to the solvent or radiation in addition to inhibition of adhesion of cells.

If necessary, the conventionally known sterilization treatment such as γ ray, ethylene oxide, an autoclave may be applied to sterilize the coated vessel.

<<Producing Method of Cell Aggregate>>

The third embodiment of the present invention is directed to a method for producing a cell aggregate comprising using the cell culture vessel of the present invention and the cell culture vessel obtained by the manufacturing method of the present invention (in the following, the both are referred to "a cell culture vessel of the present invention"). When the cell culture vessel of the present invention is used, adhesion of the cell aggregate to the surface (wall surface) of the vessel can be inhibited, and elution of the coating to the culture solution is inhibited, so that the cell aggregate can be cultured in the state without stimulation from the vessel. The cell aggregate is preferably cultured by using a medium which comprises a polysaccharide (in particular, deacylated gellan gum) having an effect of floating the cells or the tissues in the cell culture vessel of the present invention. Specific composition of such a medium or a culturing method is disclosed in, for example, WO 2014/017513A.

EXAMPLES

In the following, Synthetic examples, Examples and Test examples in connection with the culture vessel and the method for manufacturing the same of the present invention are shown, but these are shown to explain the present invention in more detail, and the present invention is not limited by these.

<Measurement Method of Raw Material Composition>

Measurement of a concentration (% by mass) of each phosphorus-containing compound in a raw material containing a phosphorus-containing compound was carried out by $^{31}$P-NMR. By using the following standard substance, absolute concentrations (absolute % by mass) of each phosphorus-containing compound contained in the raw material was calculated.

(Measurement Conditions)

Mode: Reverse gate decoupling mode (quantitative mode)
Device: Varian 400 MHz
Solvent: $CD_3OD$ (deuterated methanol) (30% by weight)
Rotation number: 0 Hz
Data point: 64,000
Flip angle: 90°
Waiting time: 70 s
Integration times: 16 times, n=4, Standard substance: trimethylphosphate+$D_2O$ (75% TMP solution was prepared)

Synthetic Example 1

Preparation of Surface Treatment Agent L1

12.40 g of pure water was added to 6.00 g of acid phosphoxyethyl methacrylate (Product name; Phosmer M, available from Unichemical Co., Ltd., a non-volatile component by the dryness method at 100° C. for 1 hour: 91.8%, a mixture of acid phosphoxyethyl methacrylate (44.2% by mass), bis[2-(methacryloyloxy)ethyl]phosphate (28.6% by mass) and other substances (27.2% by mass)) and sufficiently dissolved, then, 12.40 g of ethanol, 4.12 g of 2-(dimethylamino)ethyl methacrylate (available from Tokyo Chemical Industry Co., Ltd.) and 0.10 g of 2,2'-azo(2-methyl-N-(2-hydroxyethyl)propionamide) (Product name; VA-086, available from Wako Pure Chemical Industries, Ltd.) were further successively added thereto while maintaining at 20° C. or lower, which mixture was introduced into a dropping funnel. On the other hand, 471.13 g of pure water and 37.20 g of ethanol were charged into a three-necked flask equipped with a condenser, this was subjected to nitrogen flow, and raised to a reflux temperature while stirring. While maintaining this state, the dropping funnel into which the mixed solution had been introduced was set, and the mixed solution was added dropwise into the boiled solution of pure water and ethanol over 0.5 hour. After the dropping addition, the mixture was stirred under heating while maintaining the circumstance for 24 hours to obtain 506.05 g of a transparent polymer solution with a solid content of about 2% by mass. A weight average molecular weight of the obtained transparent liquid by GFC was about 810,000. Thereafter, to 1.00 g of the varnish containing the copolymer were added 0.9 g of pure water and 0.1 g of ethanol, and the mixture was thoroughly stirred to obtain a surface treatment agent L1 (solid content: 1% by mass).

Synthetic Example 2

Preparation of Surface Treatment Agent L2

68.88 g of pure water was added to 10.00 g of acid phosphoxyethyl methacrylate (Product name; Phosmer M, available from Unichemical Co., Ltd., a non-volatile component by the dryness method at 100° C. for 1 hour: 91.8%, a mixture of acid phosphoxyethyl methacrylate (44.2% by mass), bis[2-(methacryloyloxy)ethyl]phosphate (28.6% by mass) and other substances (27.2% by mass)) and sufficiently dissolved, then, 29.52 g of ethanol, 7.63 g of 2-(dimethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added thereto while maintaining at 20° C. or lower, which mixture was introduced into a dropping funnel. On the other hand, 373.89 g of pure water and 29.52 g of ethanol were charged into a three-necked flask equipped with a condenser, this was subjected to nitrogen flow, and raised to a reflux temperature while stirring. While maintaining this state, the dropping funnel into which the mixed solution had been introduced was set to the three-necked flask, and the mixed solution was added dropwise into the boiled solution of pure water and ethanol over 0.5 hour. After the dropping addition, the mixture was stirred under heating while maintaining the circumstance for 24 hours to obtain 509.60 g of a transparent polymer solution with a solid content of about 3.5% by mass. A weight average molecular weight of the obtained transparent liquid by GFC was about 280,000. Thereafter, to 1.00 g of the varnish containing the copolymer were added 1.56 g of pure water and 0.94 g of ethanol, and the mixture was thoroughly stirred to obtain a surface treatment agent L2 (solid content: 1% by mass).

Example 1

The following each treatment process was carried out in this order to prepare a cell culture vessel of the present invention.

Treatment 1: The surface treatment agent (L1 or L2) prepared in Synthetic example 1 or 2 was filtered by using a filter having a mesh size of 0.22 μm, added to wells of a 96-well cell culture plate (see the following Test example) to become 200 μL (solid content: 1% by mass)/well, and after allowing to stand at room temperature for 1 hour, and the excess surface treatment agent was removed.

Treatment 2: By using an oven (manufactured by Advantec Toyo Kaisha Ltd., a dryer FC-612), the material was dried at 50° C. for overnight.

Treatment 3: γ ray sterilization

<Method-1>: Normal Conditions

The coated 96-well titer plate was charged in a gas impermeable vessel with a chuck comprising an aluminum/PET laminated film having light shielding, moisture proofing and oxygen barrier properties (Product name; Lamizip AL-22, available from Seisannipponsha Ltd.), sealed under atmospheric pressure, and after allowing to stand for about 24 hours or longer, gamma ray was irradiated with 15 kGy to sterilize the vessel.

<Method-2>: Vacuum Conditions

The coated 96-well titer plate was charged in a gas impermeable vessel with a chuck comprising an aluminum/PET laminated film having light shielding, moisture proofing and oxygen barrier properties (Product name; Lamizip AL-22, available from Seisannipponsha Ltd.), sealed by heating under vacuum using a vacuum sealer, and after allowing to stand for about 24 hours or longer, gamma ray was irradiated with 15 kGy to sterilize the vessel.

<Method-3>: Antioxidant and Drying Agent Included Vacuum Conditions

The coated 96-well titer plate, a drying agent (Product name; silica gel Mix, available from Toyotakako Co., Ltd.) and a deoxidizing agent (Product name; Sequl AP-500, available from Nisso Fine Co., Ltd.) were charged in a gas impermeable vessel with a chuck comprising an aluminum/PET laminated film having light shielding, moisture proofing and oxygen barrier properties (Product name; Lamizip AL-22, available from Seisannipponsha Ltd.), sealed by heating under vacuum using a vacuum sealer, and after allowing to stand for about 24 hours or longer, gamma ray was irradiated with 15 kGy to sterilize the vessel.

Treatment 4: To each well was added 200 of ultrapure water (Milli-Q water) permeated a filter having a mesh size of 0.22 μm, then, the whole amount was removed. This treatment was carried out three times.

Test Example 1

Cell Adhesion Inhibiting Effect 1 of Cell Culture Plate to which Surface Treatment Agent was Coated (Preparation of Coating Plate)

According to the coating method shown in Example 1, wells of a flat bottom 96-well cell culture plate (manufactured by BD Biosciences, #351172) were coated by the surface treatment agent L1 or L2. At this time, as the γ ray sterilization method, <Method-1> was used. As a negative control, a plate which has not been subjected to the coating treatment was used. As a sample of the positive control, commercially available cell low adhesion plate (manufactured by Corning Incorporated, #3474) was used.

(Preparation of Cells)

The cells used were human embryonal kidney cell line Hek293 (available from DS Pharma Biomedical Co., Ltd.), human liver cancer cell line HepG2 (available from DS Pharma Biomedical Co., Ltd.) and mouse macrophage cell line RAW264.7 (available from DS Pharma Biomedical Co., Ltd.).

The medium used for culture of these cells were Hek293: an EMEM medium containing 10% (v/v) FBS (available from Wako Pure Chemical Industries, Ltd.), HepG2: a DMEM medium containing 10% (v/v) FBS (available from Wako Pure Chemical Industries, Ltd.), and RAW264.7: a DMEM/F-12 medium containing 10% (v/v) FBS (available from Sigma-Aldrich Corporation). The cells were stationary cultured in a $CO_2$ incubator at 37° C. in the state of maintaining a 5% carbon dioxide concentration by using a culture dish having a diameter of 10 cm (medium: 10 mL) for 2 days or longer. Subsequently, these cells were washed with 5 ml of PBS, 1 mL of a trypsin-EDTA solution (available from Invitrogen Corporation) was added thereto to peel off the cells, and the cells were each suspended in 10 mL of the above-mentioned medium. This suspension was centrifuged (manufactured by Kubota Corporation, model number: 5,900, 1,500 rpm/3 minutes at room temperature), the supernatant was removed, and the above-mentioned medium was added to prepare a cell suspension.

(Cell Adhesion Test)

To the plates prepared as mentioned above was each added 100 μL of the respective cell suspensions so as to be $2 \times 10^4$ cells/well. Thereafter, in the state of maintaining a 5% carbon dioxide concentration, it was allowed to stand in a $CO_2$ incubator at 37° C. for 4 days.

(Observation of Adhesion of Cells)

After 4 days from initiating the culture, adhesion of the cells to the flat bottom 96-well titer plate coated by the surface treatment agent L1 or L2, the negative control and the positive control were observed by an inverted microscope (manufactured by Olympus Corporation, CKX31) and compared to each other based thereon. The results are shown in the following Table 1. Also, as a representative example of the cell observation, a microscopic photograph (magnification: 40-fold) of the HepG2 cell cultured by the plate coated by the surface treatment agent L1 was shown in FIG. 1.

TABLE 1

| | Adhesion of cells to well | | |
|---|---|---|---|
| Plate | Hek293 cell | HepG2 cell | RAW264.7 cell |
| L1 treatment | None | None | None |
| L2 treatment | None | None | None |
| Negative control | Present | Present | Present |
| Positive control | None | None | None |

Figure 1:
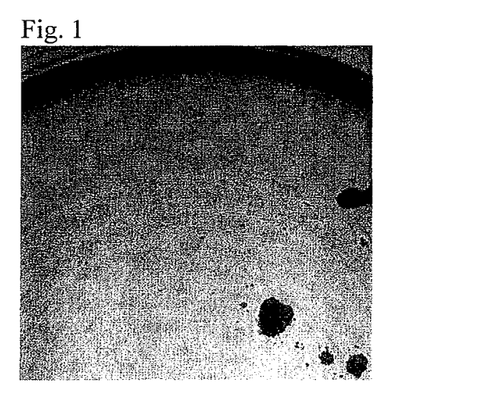
FIG. 1 shows a microscopic photograph (magnification: 40-fold) of an aggregate of HepG2 cells cultured in a flat bottom plate coated by the surface treatment agent L1 obtained in Test example 1.

As can be seen from Table 1 and FIG. 1, the plate to which L1 or L2 treatment has been applied showed that no cell was adhered in any of the cells similarly to the case of the positive control. At this time, as shown in FIG. 1, the cells which had not adhered formed a cell aggregate (spheroid).

Test Example 2

Cell Adhesion Inhibiting Effect 2 of Cell Culture Plate to which Surface Treatment Agent was Coated (Preparation of Coating Plate)

According to the coating method shown in Example 1, wells of a flat bottom 96-well cell culture plate (manufactured by BD Biosciences, #351172) were coated by the surface treatment agent L1. At this time, as the γ ray sterilization method, <Method-1>, <Method-2> and <Method-3> were used. As a negative control, a plate which has not been subjected to the coating treatment was used.

(Preparation of Cell)

The cell used was human embryonal kidney cell line Hek293 (available from DS Pharma Biomedical Co., Ltd.). For the culture of this cell, an EMEM medium containing 10% (v/v) FBS (available from Wako Pure Chemical Industries, Ltd.) was used. The cells were stationary cultured in a $CO_2$ incubator at 37° C. in the state of maintaining a 5% carbon dioxide concentration by using a culture dish having a diameter of 10 cm (medium: 10 mL) for 2 days or longer. Subsequently, these cells were washed with 5 ml of PBS, 1 mL of a trypsin-EDTA solution (available from Invitrogen Corporation) was added thereto to peel off the cells, and the cells were each suspended in 10 mL of the above-mentioned medium. This suspension was centrifuged (manufactured by Kubota Corporation, model number: 5,900, 1,500 rpm/3 minutes at room temperature), the supernatant was removed, and the above-mentioned medium was added to prepare a cell suspension.

(Cell Adhesion Test)

To the plates prepared as mentioned above was each added 100 μL of the Hek293 cell suspension so as to be $2 \times 10^4$ cells/well. Thereafter, in the state of maintaining a 5% carbon dioxide concentration, it was allowed to stand in a $CO_2$ incubator at 37° C. for 4 days.

(Observation of Adhesion of Cells)

After 4 days from initiating the culture, adhesion of the cells to the flat bottom 96-well titer plate coated by the surface treatment agent L1 and the negative control were observed by an inverted microscope (manufactured by Olympus Corporation, CKX31) and compared to each other based thereon. The results are shown in the following Table 2.

TABLE 2

| | γ ray sterilization method | | | |
|---|---|---|---|---|
| | <Method-1> | <Method-2> | <Method-3> | Negative control |
| Adhesion of cells to well | None | None | None | Present |

As shown in Table 2, it was shown that the plate which has been subjected to the γ ray sterilization treatment after applying the L1 treatment showed that no Hek293 cell was adhered. At this time, the cells which had not adhered formed a cell aggregate (spheroid) in the well.

Test Example 3

Cell Adhesion Inhibiting Effect 3 of Cell Culture Plate to which Surface Treatment Agent was Coated (Preparation of Coating Plate)

According to the coating method shown in Example 1, wells of a U-letter shaped bottom 96-well cell culture plate (manufactured by BD Biosciences, #353227) were coated by the surface treatment agent L1 or L2. At this time, γ ray sterilization was not carried out. As a negative control, a plate which has not been subjected to the coating treatment was used. As a sample of the positive control, commercially available cell low adhesion plate (manufactured by Sumitomo Bakelite Co., Ltd., #MS-9096U) was used.

(Preparation of Cell)

The cell used was human liver cancer cell lines HepG2 (available from DS Pharma Biomedical Co., Ltd.). For the culture of this cell, DMEM medium containing 10% (v/v) FBS (available from Wako Pure Chemical Industries, Ltd.) was used. The cells were stationary cultured in a $CO_2$ incubator at 37° C. in the state of maintaining a 5% carbon dioxide concentration by using a culture dish having a diameter of 10 cm (medium: 10 mL) for 2 days or longer. Subsequently, these cells were washed with 5 ml of PBS, 1 mL of a trypsin-EDTA solution (available from Invitrogen Corporation) was added thereto to peel off the cells, and the cells were each suspended in 10 mL of the above-mentioned medium or a medium to which deacylated gellan gum with a final concentration of 0.015% (w/v) has been added to prepare the respective cell suspensions. This suspension was centrifuged (manufactured by Kubota Corporation, model number: 5,900, 1,500 rpm/3 minutes at room temperature), the supernatant was removed, and the above-mentioned medium was added to prepare a cell suspension. Here, the medium to which 0.015% (w/v) of deacylated gellan gum has been added was prepared as mentioned below. That is, the deacylated gellan gum (KELCOGEL CG-LA, available from Sansho Co., Ltd.) was suspended in ultra-pure water (Milli-Q water) so that it became 0.3% (w/v), then, dissolved by stirring while heating to 90° C., and this aqueous solution was sterilized in an autoclave at 121° C. for 20 minutes. This solution was added to a DMEM medium (available from Wako Pure Chemical Industries, Ltd.) containing 10% (v/v) FBS so that the deacylated gellan gum became a final concentration of 0.015% (w/v) while stirring well.

(Cell Adhesion Test)

To the plates prepared as mentioned above was each added 100 μL of the respective cell suspensions so as to be $2 \times 10^3$ cells/well. Thereafter, in the state of maintaining a 5% carbon dioxide concentration, it was allowed to stand in a CO₂ incubator at 37° C. for 5 days.

(Observation of Adhesion of Cells)

After 5 days from initiating the culture, adhesion of the cells to the U-letter shaped bottom 96-well titer plate coated by the surface treatment agent L1 or L2, the negative control and the positive control were observed by an inverted microscope (manufactured by Olympus Corporation, CKX31) and compared to each other based thereon. The results are shown in the following Table 3. Also, as a representative example of the cell observation, a microscopic photograph (magnification: 40-fold) of the HepG2 cell cultured by the plate coated by the surface treatment agent L1 was shown in FIG. 2.

TABLE 3

| | Adhesion of cells to well | |
|---|---|---|
| Plate | No deacylated gellan gum | Deacylated gellan gum present |
| L1 treatment | None | None |
| L2 treatment | None | None |
| Negative control | Present | Present |
| Positive control | None | Not carried out |

Figure 2:
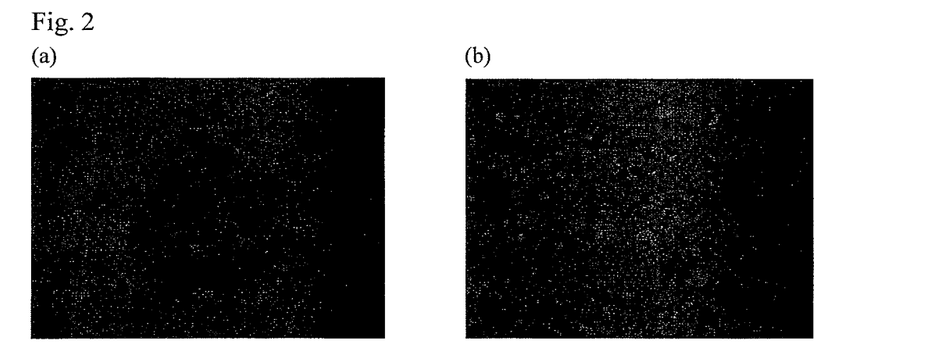

As shown in Table 3 and FIG. 2, the plates to which L1 or L2 treatment has been applied showed that no cell was adhered in any of the cells similarly to the case of the positive control. At this time, as shown in FIG. 2, the cells which had not adhered formed a cell aggregate (spheroid) at the neighbor of the center portion at the bottom of the well. Further, when a medium to which the deacylated gellan gum has been added was used, it has been shown that a size of the cell aggregate was small as compared with the case to which the same has been not added, and yet it was dispersed.

UTILIZABILITY IN INDUSTRY

The cell culture vessel of the present invention is coated by a copolymer containing a specific organic group at least a part of the surface thereof. Such a coating inhibits adhesion of the cells to the surface (wall surface) of the vessel as well as the coating can be firmly fixed to the surface of the vessel, so that elution of the coating to the culture solution is suppressed and radiation resistance is improved. Accordingly, the cell culture vessel of the present invention is advantageous in the point of culturing a cell aggregate in the state without stimulation from the vessel.

The invention claimed is:

1. A cell culture vessel comprising a surface coating of a varnish comprising a copolymer present in an amount of 0.01 to 4% by mass in a solvent mixture selected from an alcohol and water or an alcohol and phosphate buffered saline,
    wherein the varnish is coated onto at least part of a surface of the vessel so that the at least part of the surface of the vessel is maintained to be electrically neutral by an electrostatic balance between anionic and cationic charges associated with the copolymer,
    wherein the electrostatic balance of the copolymer in the varnish is maintained by adding a pH adjusting agent to the varnish to make the pH of the varnish from 3.5 to 8.5,
    wherein the copolymer in the varnish inhibits adhesion of cells to the surface of the vessel onto which the varnish is coated,
    wherein the copolymer contains a recurring unit containing an organic group of the following formula (a) and a recurring unit containing an organic group of the following formula (b):

wherein $U^{a1}$ and $U^{a2}$ are each hydrogen, $U^{b1}$, $U^{b2}$, and $U^{b3}$ each independently represent hydrogen or a linear or branched alkyl group having 1 to 5 carbon atoms, and $An^-$ represents an anion selected from the group consisting of a halide ion, an inorganic acid ion, a hydroxide ion, and an isothiocyanate ion, and
    wherein the varnish with the pH adjusted to maintain the electrostatic balance between anionic and cationic charges associated with the copolymer is obtained by
copolymerizing a monomer containing the organic group of formula (a) and a monomer containing the organic group of formula (b) at 50° C. to 200° C. to provide a copolymer,
combining the resultant copolymer in an amount of 0.01 to 4% by mass with a solvent mixture selected from an alcohol and water or an alcohol and phosphate buffered saline to provide the varnish, and
adjusting the pH of the resultant varnish to between 3.5 and 8.5 to maintain the electrostatic balance between anionic and cationic charges associated with the copolymer.

2. The cell culture vessel according to claim 1, wherein the recurring units containing organic groups of the above-mentioned formulae (a) and (b) are recurring units derived from monomers of the following formulae (A) and (B), respectively:

wherein $U^{a1}$ and $U^{a2}$ are each hydrogen, $T^a$, $T^b$, $U^{b1}$, $U^{b2}$, and $U^{b3}$ each independently represent hydrogen or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which are optionally substituted by a halogen atom(s), $An^-$ represents an anion selected from the group consisting of a halide ion, an inorganic acid ion, a hydroxide ion, and an isothiocyanate ion, and m is an integer of 0 to 6.

3. The cell culture vessel according to claim 2, wherein m is 1, and $R^a$ and $R^b$ each independently represent an ethylene group or a propylene group.

4. The cell culture vessel according to claim 1, wherein the copolymer further contains a crosslinked structure derived from a monomer of the following formula (C) or (D):

wherein $T^c$, $T^d$, and $U^d$ each independently represent hydrogen or a linear or branched alkyl group having 1 to 5 carbon atoms, and $R^c$ and $R^d$ each independently represent a linear or branched alkylene group having 1 to 10 carbon atoms which are optionally substituted by a halogen atom(s).

5. The cell culture vessel according to claim 4, wherein $T^c$ and $T^d$ each independently represent hydrogen or a methyl group, $U^d$ represents hydrogen, and $R^c$ and $R^d$ each independently represent an ethylene group or a propylene group.

6. A method for manufacturing a cell culture vessel comprising coating a varnish that comprises a copolymer and a solvent mixture selected from an alcohol and water or an alcohol and phosphate buffered saline, wherein the varnish has a pH between 3.5 and 8.5, and wherein the concentration of the copolymer in the varnish is 0.01 to 4% by mass, onto at least part of a surface of a vessel, and drying the coated cell culture vessel at −200° C. to 200° C., wherein the copolymer contains a recurring unit containing an organic group of the following formula (a) and a recurring unit containing an organic group of the following formula (b):

wherein $U^{a1}$ and $U^{a2}$ are each hydrogen, $U^{b1}$, $U^{b2}$, and $U^{b3}$ each independently represent hydrogen or a linear or branched alkyl group having 1 to 5 carbon atoms and $An^-$ represents an anion selected from the group consisting of a halide ion, an inorganic acid ion, a hydroxide ion, and an isothiocyanate ion.

7. The manufacturing method according to claim 6, wherein the recurring units containing organic groups of the formulae (a) and (b) are recurring units derived from monomers of the following formulae (A) and (B), respectively:

wherein $U^{a1}$ and $U^{a2}$ are each hydrogen, $T^a$, $T^b$, $U^{b1}$, $U^{b2}$, and $U^{b3}$ each independently represent hydrogen or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which are optionally substituted by a halogen atom(s), $An^-$ represents an anion selected from the group consisting of a halide ion, an inorganic acid ion, a hydroxide ion, and an isothiocyanate ion, and m is an integer of 0 to 6.

8. The manufacturing method according to claim 6, further comprising adjusting the pH of the varnish prior to the coating process.

9. The manufacturing method according to claim 6, wherein the method further comprises a process of washing the coated cell culture vessel before and/or after the drying process.

10. The manufacturing method according to claim 9, wherein the washing after the drying process is carried out by using at least one solvent selected from the group consisting of water and an aqueous solution containing an electrolyte.

11. A method for producing a cell aggregate comprising culturing cells with a cell culture vessel according to claim 1.

12. The producing method of a cell aggregate according to claim 11, wherein a medium in the cell culture vessel contains a polysaccharide having an effect of floating cells or tissues.

13. The producing method of a cell aggregate according to claim 12, wherein the polysaccharide is deacylated gellan gum.

14. A method for producing a cell aggregate comprising culturing cells with a cell culture vessel manufactured by the manufacturing method according to claim 6, wherein the pH of the varnish maintains a neutral electrostatic balance between anionic and cationic charges associated with the copolymer.

15. A method for manufacturing a cell culture vessel comprising coating a varnish that comprises a copolymer and a solvent mixture selected from an alcohol and water or an alcohol and phosphate buffered saline, wherein the varnish has a pH between 3.5 and 8.5, and wherein the concentration of the copolymer in the varnish is 0.01 to 4% by mass, onto at least part of a surface of a vessel, and drying the coated cell culture vessel at −200° C. to 200° C., wherein the cell culture vessel is coated by the varnish onto the at least part of the surface of the vessel so that the at least part of the surface of the vessel is maintained to be electrically neutral by adjusting the pH to maintain an electrostatic balance between anionic and cationic charges associated with the copolymer, and wherein the copolymer inhibits adhesion of cells to the surface of the vessel, and the copolymer contains (1) a recurring unit containing an organic group of the following formula (a) and a recurring unit containing an organic group of the following formula (b):

wherein $U^{a1}$, $U^{a2}$, $U^{b1}$, $U^{b2}$, and $U^{b3}$ each independently represent hydrogen or a linear or branched alkyl group having 1 to 5 carbon atoms, and An⁻ represents an anion selected from the group consisting of a halide ion, an inorganic acid ion, a hydroxide ion, and an isothiocyanate ion, and

(2) a crosslinked structure derived from a monomer of the following formula (C) or (D):

wherein $T^c$, $T^d$, and $U^d$ each independently represent hydrogen or a linear or branched alkyl group having 1 to 5 carbon atoms, and $R^c$ and $R^d$ each independently represent a linear or branched alkylene group having 1 to 10 carbon atoms which are optionally substituted by a halogen atom(s).

16. A method for manufacturing a cell culture vessel comprising providing a copolymer by copolymerizing a monomer containing an organic group of formula (a) and a monomer containing an organic group of formula (b):

wherein $U^{a1}$ and $U^{a2}$ are each hydrogen, $U^{b1}$, $U^{b2}$, and $U^{b3}$ each independently represent hydrogen or a linear or branched alkyl group having 1 to 5 carbon atoms, and An⁻ represents an anion selected from the group consisting of a halide ion, an inorganic acid ion, a hydroxide ion, and an isothiocyanate ion, combining the copolymer and a solvent mixture selected from an alcohol and water or an alcohol and phosphate buffered saline to provide a varnish, wherein the concentration of the copolymer in the varnish is 0.01 to 4% by mass, adjusting the pH of the varnish to between 3.5 and 8.5, coating the varnish onto at least part of a surface of a vessel to provide a coated cell culture vessel, and drying the coated cell culture vessel at 50° C. to 200° C., wherein the cell culture vessel is coated by the varnish onto the at least part of the surface of the vessel so that the at least part of the surface of the vessel is maintained to be electrically neutral by an electrostatic balance between anionic and cationic charges associated with the copolymer by the pH of the varnish, and the copolymer inhibits adhesion of cells to the at least part of the surface of the vessel coated with the varnish.

17. The method according to claim 16, wherein the monomers containing organic groups of the above-mentioned formulae (a) and (b) are monomers of formulae (A) and (B), respectively:

wherein $U^{a1}$ and $U^{a2}$ are each hydrogen, $T^a$, $T^b$, $U^{b1}$, $U^{b2}$, and $U^{b3}$ each independently represent hydrogen or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which are optionally substituted by a halogen atom(s), An⁻ represents an anion selected from the group consisting of a halide ion, an inorganic acid ion, a hydroxide ion, and an isothiocyanate ion, and m is an integer of 0 to 6.

18. The method according to claim 17, wherein m is 1, and $R^a$ and $R^b$ each independently represent an ethylene group or a propylene group.

19. The method according to claim 16, wherein the copolymer further comprises a crosslinked structure derived from a monomer of the following formula (C) or (D):

wherein $T^c$, $T^d$, and $U^d$ each independently represent hydrogen or a linear or branched alkyl group having 1 to 5 carbon atoms, and $R^c$ and $R^d$ each independently represent a linear or branched alkylene group having 1 to 10 carbon atoms which are optionally substituted by a halogen atom(s).

20. The method according to claim 19, wherein $T^c$ and $T^d$ each independently represent hydrogen or a methyl group, $U^d$ represents hydrogen, and $R^c$ and $R^d$ each independently represent an ethylene group or a propylene group.

21. The cell culture vessel of claim 1, wherein the alcohol is selected from the group consisting of ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol, 2-methyl-1-propanol, 2-methyl-1-butanol, 2-methyl-2-butanol, 3-methyl-1-butanol, 3-methyl-3-pentanol, cyclopentanol, 1-hexanol, 2- hexanol, 3-hexanol, 2,3-dimethyl-2-butanol, 3,3 -dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol.

22. The method of claim 6, wherein the alcohol is selected from the group consisting of ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol, 2-methyl-1-propanol, 2-methyl-1-butanol, 2-methyl-2-butanol, 3-methyl-1-butanol, 3-methyl-3-pentanol, cyclopentanol, 1-hexanol, 2-hexanol, 3-hexanol, 2,3-dimethyl-2-butanol, 3,3 -dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol.

23. The method of claim 15, wherein the alcohol is selected from the group consisting of ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol, 2-methyl-1-propanol, 2-methyl-1-butanol, 2-methyl-2-butanol, 3-methyl-1-butanol, 3-methyl-3-pentanol, cyclopentanol, 1-hexanol, 2-hexanol, 3-hexanol, 2,3-dimethyl-2-butanol, 3,3 -dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol.

24. The method of claim 16, wherein the alcohol is selected from the group consisting of ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol, 2-methyl-1-propanol, 2-methyl-1-butanol, 2-methyl-2-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, and cyclohexanol.

* * * * *